(12) United States Patent
Slater (10) Patent No.: US 7,023,545 B2
(45) Date of Patent: Apr. 4, 2006

(54) CHEMICAL IDENTIFICATION BY FLASH SPECTROSCOPY

(75) Inventor: Richard C. Slater, Waban, MA (US)

(73) Assignee: Textron Systems Corporation, Wilmington, MA (US)

( * ) Notice: Subject to any disclaimer, the term of this patent is extended or adjusted under 35 U.S.C. 154(b) by 322 days.

(21) Appl. No.: 10/460,101

(22) Filed: Jun. 12, 2003

(65) Prior Publication Data

US 2004/0252300 A1 Dec. 16, 2004

(51) Int. Cl.
*G01J 3/28* (2006.01)

(52) U.S. Cl. ...................................... 356/326
(58) Field of Classification Search ................ 356/326, 356/328; 372/72
See application file for complete search history.

(56) References Cited

U.S. PATENT DOCUMENTS

| | | | |
|---|---|---|---|
| 4,349,907 A | 9/1982 | Campillo et al. | |
| 5,047,668 A | 9/1991 | Bosenberg | |
| 5,144,630 A | 9/1992 | Lin | |
| 5,241,179 A | 8/1993 | Carrieri | |
| 5,657,119 A | 8/1997 | Kawasaki et al. | |
| 6,060,710 A | 5/2000 | Carrieri et al. | |
| 6,075,252 A * | 6/2000 | Atkinson et al. | 250/559.4 |
| 6,289,027 B1 | 9/2001 | Lawrence et al. | |
| 6,445,449 B1 | 9/2002 | Sharts et al. | |
| 2002/0155541 A1 | 10/2002 | Naughton et al. | |
| 2002/0176454 A1 | 11/2002 | Arbore et al. | |
| 2002/0176472 A1 | 11/2002 | Arbore et al. | |
| 2004/0024540 A1* | 2/2004 | Bove et al. | 702/28 |

FOREIGN PATENT DOCUMENTS

WO      WO 93/11424      6/1993

OTHER PUBLICATIONS

Chen et al. "Multiplex coherent anti-Stokes Raman spectroscopy by use of a nearly degenerate broadband optical parametric oscillator", Sep. 20, 1999, Applied Optics, vol. 38, No. 27, pp. 5894-5898.*

Cheung et al., "High Power Optical Parametric Oscillator Source," IEEE, vol. 3, Mar. 18, 2000, pp. 55-59.

(Continued)

*Primary Examiner*—Gregory J. Toatley, Jr.
*Assistant Examiner*—Kara Geisel
(74) *Attorney, Agent, or Firm*—Lesley A. Hamlin (57) ABSTRACT

A light source produces a pump wave that is used to pump a parametric device. The parametric device is configured at or near its degeneracy point and produces a broadband output. The broadband output is directed to a remote location where chemical agents may be located. The broadband output may be transmitted through or scattered from the remote location and chemical agents located at the remote location may absorb portions of the broadband output. The broadband output may be collected and dispersed to produce channels or sub-bands that are detected by a detector array. The detector array may multiplex the intensities of the sub-bands and produce an absorption spectrum. The absorption spectrum may be compared to a library of known chemical agents and the presence of a chemical agent at the remote location can be determined in or near real time.

44 Claims, 5 Drawing Sheets

OTHER PUBLICATIONS

Appel et al., "Ladar Using Broadband Optical Source," Proceedings of the SPIE—The Int'l Soc. for Optical Eng'g SPIE-INT. Soc. Opt. Eng USA, vol. 3380, 1998, pp. 97-106.

Gordienko et al., "New Potentialities of a Broadband . . . ," Quantum Electronics Turpion Ltd., Kvantovaya Elektronika, UK, vol. 30, No. 9, Sep. 1, 2000, pp. 839-842.

Gillespie et al., "Development of a Broadband Lidar System . . . ," Measurement Science and Technology, IOP Publishing, Bristol, GB, vol. 13, No. 3, Mar. 2002, pp. 383-390.

Phua et al., "Oscillation threshold of Pulsed Doubly . . . ," Optics Communications, North-Holland Pub. Co., Amsterdam, NL, vol. 139, No. 4-6, Jul. 1, 1997, pp. 320-326.

Sung-Huan, Gong, "Generation of a Broad-band Picosecond . . . ," Journal of the Korean Physical Society Korean Phys. Soc South Korea, vol. 41, No. 5, Nov. 2002, pp. 699-705.

Chih-Wei et al., "Retracing Behavior and Broadband . . . ," Jour. of the Optical Soc. of America B (Optical Physics) Opt. Soc. America USA, vol. 19, No. 5, May 2002, pp. 1150-1156.

Remote Sensing Section, U.S. Army Chemical Systems Laboratory, "Atlas of Infrared Spectra (8-13 uM) of Chemical Agents and Potential Interferences," (Mar. 29, 1977).

Gittins et al., "Remomte Characterization of Chemical Vapor Plumes by LWIR Imaging Fabry-Perot Spectrometry," Physical Sciences Inc., p. 1-13, (Sep. 24, 2001).

Gittins et al., "Passive and Active Standoff Infrared Detection of Bio-Aerosols," Field Analytical Chemistry and Technology, John Wiley & Sons, Inc., p. 1-25, (1999).

K.L. Vodopyanov, "Mid-infrared optical parametric generator with extra-wide (3-19 um) tunability: applications for spectroscopy of two-dimensional electrons in quantum wells," Journal of Optical Society of America, Optical Society of America, vol. 16 (No. 9), p. 1579-1586, (Sep. 1999).

Sonnenfroh et al., "Pollutant emission monitoring using QC laser-based mid-IR sensors," Proceedings of SPIE, vol. 4199, Society of Photo-Optical Instrumentation Engineers, (2001).

Frish et al., "Handheld laser-based sensor for remote detection of toxic and hazardous gases," SPIE Paper No. 4199-05, Society of Photo-Optical Instrumentation Engineers, (Nov. 5, 2000).

Gittins et al., "Quantitative Gas Sensing by Backscatter-Absorption Measurements of a Pseudo-Random Code Modulated 8 um Quantum Cascade Laser," Optics Letters, Optical Society of America, vol. 25 (No. 16), p. 1162-1164, (Aug. 15, 2000).

Ross et al., "Principles and possibilities for optical parametric chirped pulse amplifiers," CLF Annual Report—1997/98, CLRC Rutherford Appleton Laboratory (<http://www.clf.rl.ac.uk/Reports/1997-1998/pdf/77.pdf>), p. 169-172.

Dieter H. Jundt, "Temperature-dependent Sellmeier equation for the index of refraction, ne, in congruent lithium niobate," Optics Letters, Optical Society of America, vol. 22 (No. 20), p. 1553-1555, (Oct. 15, 1997).

Walther et al., "Collective Vibrational Modes in Biological Molecules Investigated by Terahertz Time-Domain Spectroscopy," Wiley InterScience, Inc. (<http://www.interscience.wiley.com>), p. 310-313, (Apr. 26, 2002).

Anatoliy A. Kosterev and Frank K. Tittel, "Chemical Sensors Based on Quantum Cascade Lasers," IEEE Journal of Quantum Electronics, IEEE, vol. 38 (No. 6), p. 582-591, (Jun. 2002).

N. Dietz and F.L. Madarasz, "Chemical and biological sensors based on optically confined birefringent chalcopyrite heterostructures," Materials Science and Engineering B97, Elsevier Science B. V., p. 182-195, (2003).

Christesen et al., "Surface Enhanced Raman Detection and Identification of Chemical Agents in Water," US Army Edgewood Chemical Biological Center (<http://www.asc2002.com/summaries/g/GP-04.pdf>), (2002).

Beddard et al., "Five-optical-cycle pulse generation in the mid infrared from an optical parametric oscillator based on aperiodically poled lithium niobate," Optics Letters, Optical Society of America, vol. 25 (No. 14), p. 1052-1054, (Jul. 15, 2000).

Hoyt et al., "High-power picosecond optical parametric oscillator based on periodically poled lithium niobate," Optical Letters, Optical Society of America, vol. 27 (No. 17), p. 1543-1545, (Sep. 1, 2002).

McGowan et al., "Femtosecond optical parametric oscillator based on periodically poled lithium niobate," Journal of Optical Society of America, Optical Society of America, vol. 15 (No. 2), p. 694-701, (Feb. 1998).

Kartaloglu et al., "Femtosecond optical parametric oscillator based on periodically poled KTiOPO4," Optics Letters, Optical Society of America, vol. 23 (No. 1), p. 61-63, (Jan. 1, 1998).

Hofstetter et al., "High Average Power First-Order Distributed Feedback Quantum Cascade Lasers," IEEE Photonics Technology Letters, IEEE, vol. 12 (No. 12), p. 1610-1612, (Dec. 2000).

Vodopyanov et al., "ZnGeP optical parametric oscillator with 3.8-12.4-uM tunability," Optical Letters, Optical Society of America, vol. 25 (No. 11), p. 841-843, (Jun. 1, 2000).

Kim et al., "Tuning Characteristics of a Continuous-Wave KTP Optical Parametric Oscillator," Journal of the Korean Physical Society, vol. 34 (No. 3), p. 227-230, (Mar. 1999).

Albert Tebo, "Uncooled IR detectors: their time has come," SPIE—The International Society for Optical Engineering (<http://www.spie.org/web/oer/october96/uncoolir.html>), p. 1-5.

Bortz et al., "Quasi-phase-matched optical parametric amplification and oscillation in periodically poled LiNbO waveguides," Optics Letters, Optical Society of America, vol. 20 (No. 1), p. 49-51, (Jan. 1, 1995).

K. Osvay and I.N. Ross, "Optical parametric chirped pulse amplification—experimental progress," CLF Annual Report—1997/98, CLRC Rutherford Appleton Laboratory (<http://www.clf.rl.ac.uk/Reports/1997-1998/contents.html>), p. 173-174.

Galvanauskas et al., "Fiber-laser-based femtosecond parametric generator in bulk periodically poled LiNbO," Optics Letters, Optical Society of America, vol. 22 (No. 2), p. 105-107, (Jan. 15, 1997).

Artigas et al., "Pulse compression and gain enhancement in a degenerate optical parametric amplifier based on aperiodically poled crystals," Optics Letter, Optical Society of America, vol. 27 (No. 6), p. 442-444, (Mar. 15, 2002).

Ino, "IRL 256 B—Uncooled IR Bolometric Detector," http://www.nightlaser.com/pdf/IRL256B.pdf>, (Nov. 2000).

* cited by examiner

CHEMICAL IDENTIFICATION BY FLASH SPECTROSCOPY

BACKGROUND

Chemical compounds may be identified by spectral techniques, which may be classified broadly by the type of energy that is used. Such techniques may be referred to as "light spectroscopy" when photons are used, "electron" or "Auger" spectroscopy when electrons are used, and "mass spectroscopy" when ions are used. Spectral or spectroscopic techniques in general require an energy source and a device for measuring the change in the energy of the source after the energy has interacted with a sample or chemical compound. Light spectroscopy may be classified by the type of optical light that is produced by the light source, i.e., infrared or "IR" spectroscopy, "visible" spectroscopy, and, ultraviolet or "UV" spectroscopy. For light spectroscopy, lasers and arc lamps are commonly used as energy sources and spectrometers and interferometers are often used as the measuring device.

Depending on the type of energy source used, light spectroscopy may be further classified as being passive or active. Passive light spectroscopy uses the inherent thermal radiance of a material as a radiation source, while active light spectroscopy uses a light source to illuminate a region of interest. Active spectroscopic techniques may detect and measure light that has been reflected or scattered from or transmitted through a target or region that contains a gas, a liquid, or a solid. These techniques include various "absorption" techniques that in general detect the percentage difference between light that is incident on a target or sample and light that is transmitted or reflected from that target or sample.

For absorption spectroscopy, energy in the form of flux photons from a light source is directed to and incident on a sample, region or target. Molecules within the sample, region or target may absorb light at particular frequencies, and different molecules may absorb energy more readily at certain frequencies than at others. Within a given molecule, bonds between atoms or groups of atoms, or "functional groups," may have characteristic stretching, bending and twisting resonant frequencies. Any given chemical will absorb energy at such resonant frequencies and tend not to absorb energy at other non-resonant frequencies. Light from a source that is incident on and reflected from or transmitted through a chemical will contain an absorption spectrum or "chemical fingerprint" that is characteristic of that particular chemical. Different chemicals have different absorption spectra and characteristic features, e.g., peaks and valleys, may exist across the optical spectrum from the far ultra violet (FUV), through the visible region, to the far or long wave infrared (LW IR). Many chemical absorption spectra are known and such absorption spectra may be found in many chemical literature references.

Absorption spectroscopic techniques can be used to detect chemicals at remote locations because there are certain optical transmission bands or "windows" in the atmosphere. These windows exist because the gas molecules of the atmosphere have their own absorption spectra and absorb light at certain wavelengths and frequencies and not at others. Consequently, certain optical wavelengths are unsuited for absorption spectroscopy while certain others are well suited for such use. For example, infrared (IR) transmission windows exist in wavelength ranges between 3 and 5 microns and between 8 and 12 microns, as well as others.

Active light spectroscopy techniques have been used previously for the detection of chemical agents at a distance. However, these techniques have utilized the tuning of a light source across a wavelength spectrum. Active optical spectroscopy systems that have been used to identify chemicals at a remote location have typically done so by tuning a laser source, e.g., a tunable diode laser (TDL), through a range of wavelengths and by detecting the absorption for each tuned wavelength. The incorporation of such tuning slows the chemical identification process. The necessary tuning across the spectral range of interest takes a period of time and requires additional apparatus of added complexity, size and expense.

Passive light spectroscopy techniques have also been used to detect chemicals at a distance. These are slower than active systems because of the time required to detect thermally emitted radiation or scatted and diffuse light. Additionally, the lack of an illumination source in such systems leads to inconsistent and unreliable light detection and further necessitates detection over long periods of time. The Joint Service Lightweight Standoff Chemical Agent Detector (JSLSCAD) used by the U.S. Armed Forces is an example of such a passive optical spectroscopic system. In addition, passive systems such as the Joint Service Lightweight Standoff Chemical Agent Detector are subject to high false alarms rates due to the low signal-to-noise ratio (S/N) of the detected thermal radiation and dark current noise within the detectors of the passive system.

Nonlinear optics have been used to generate light at certain wavelength ranges in which laser sources are not available, e.g., due to a lack of lasing or active media generating light in those wavelength ranges at sufficient power levels. Nonlinear optics techniques include optical parametric generation, which involves the mixing of three optical waves or fields within a nonlinear crystal. A degeneracy point occurs when two of the three waves have the same or nearly the same energy or frequency (and consequently, wavelength). Information related to attempts to tuning a parametric oscillator through the degeneracy point can be found in U.S. Pat. No. 4,349,907, U.S. Pat. Pub. No. US2002/0176454, and U.S. Pat. Pub. No. US2002/0176472. U.S. Pat. No. 4,349,907 ("'907 patent") entitled "Broadly Tunable Picosecond IR Source," published Sep. 14, 1982, discloses a picosecond traveling-wave parametric device capable of controlled spectral bandwidth and wavelength in the infrared region. The output of this system is not broadband in nature but is only tunable over a range of infrared wavelengths. Tuning over such a range is slow and is not suitable for real time or quasi real time spectroscopy.

U.S. Pat. Pub. No. US2002/0176454, entitled "Method for Tuning Nonlinear Frequency Mixing Devices Through Degeneracy," published Nov. 28, 2002, and related U.S. Pat. Pub. No. US2002/0176472, entitled "Tunable Light Source Employing Optical Parametric Oscillation Near Degeneracy," published Nov. 28, 2002, disclose the tuning of optical parametric devices through the degeneracy point to achieve an output with a wide tuning range. As with the above-referenced '907 patent, tuning by its very nature takes a certain period of time, and is therefore inherently slower than without tuning. The techniques disclosed are therefore unsuited for real time or quasi real time spectroscopy. Additionally, tuning apparatus are inherently complex and increase the size and cost of the systems they are used with.

What is needed therefore is a real time or quasi real time chemical detection system that is relatively simple and inexpensive. What is further needed is such a system that can qualitatively detect chemical agents including chemical and biological warfare agents at a remote location without the need for tuning across an output range.

SUMMARY

Briefly, and in general terms, the present invention includes systems and methods that produce a broadband output that may include one or more broad spectrum pulses or "flashes" to determine the presence of certain chemicals at a remote location. The presence of a particular chemical may be determined qualitatively. The broadband output may include wavelengths in the ultraviolet, visible, and infrared ranges.

A flash spectroscopy standoff chemical detection system includes a light source and a parametric device configured to receive a pump wave at a degeneracy point of the parametric device. The parametric device receives the pump wave from the light source and produces a broadband output. The broadband output is transmitted to a remote location where a chemical agent may be present. A spectrometer may be included that is operable to receive the broadband output from the remote location and to produce an absorption spectrum.

The broadband output may include an idler wave and a signal wave, and the idler wave may in some embodiments be substantially equal to the signal wave. In some embodiments the broadband output may have a bandwidth or linewidth with a full-width half-maximum value of about 5 percent to about 25 percent of a central wavelength of the broadband output. The broadband output may have a bandwidth or linewidth with a full-width half-maximum value of greater than 200 wave numbers per centimeter (200 cm$^{-1}$). In certain embodiments the broadband output may have a bandwidth or linewidth with a full-width half-maximum value of greater than 300 wave numbers per centimeter (300 cm$^{-1}$). The pump wave may have a wavelength that is equal to about one-half of the idler or signal wavelength. In certain embodiments, a central wavelength of one of the idler wave and the signal wave may be between about 8 microns to about 12 microns.

A method of standoff chemical detection includes supplying a pump wave to a parametric device configured at a degeneracy point and producing a broadband output. The broadband output may be directed to a remote location where a chemical agent may be located. The broadband output may be detected from the remote location and a chemical absorption spectrum of the chemical agent may be produced.

The detection of the broadband output may further include dispersing the broadband output into two or more sub-bands. An intensity of each of the two or more sub-bands may be detected and multiplexed to form the absorption spectrum. The absorption spectrum may be compared to one or more absorption spectra of known chemicals or chemical agents.

A flash spectroscopy chemical detection system includes means for producing a pump wave and means for degenerately amplifying the pump wave and producing a broadband output. The system may include means for directing the broadband output to a remote location as well as means for detecting the broadband output from the remote location. Also included are means for identifying a chemical agent.

The means for identifying a chemical agent may further include means for producing a chemical absorption spectrum and/or means for dispersing the broadband output into two or more sub-bands. The means for identifying a chemical agent may include means for detecting an intensity of each of the two or more sub-bands. The means for identifying a chemical agent may further include means for multiplexing the intensities of the two or more sub-bands to produce the absorption spectrum. The means for identifying a chemical agent may include means for comparing or correlating the absorption spectrum with a known chemical absorption spectrum. In certain embodiments, the broadband output may have a bandwidth or linewidth with a full-width half-maximum value of greater than 200 wave numbers per centimeter (200 cm$^{-1}$).

BRIEF DESCRIPTION OF THE DRAWINGS

These and other features, aspects, and advantages of the present invention will become better understood with regard to the following description, appended claims, and accompanying drawings. The drawings are not necessarily to scale, emphasis instead being placed upon illustrating the principles of the present invention. The drawings include the following:

DETAILED DESCRIPTION

The present invention may be understood by the following detailed description, which should be read in conjunction with the attached drawings. The following detailed description is by way of example only and is not meant to limit the scope of the present invention.

The present invention is directed to systems and methods that produce a broadband output, for example in the infrared region, which may be directed to a remote location to detect chemical agents. Due to the large bandwidth of the broadband output, an absorption spectrum that indicates the presence of one or more chemical agents may be produced in near real time without the need for tuning a light source. As a result, chemical agents including chemical and biological warfare agents and/or their synthetic precursors and breakdown products may be identified. The avoidance of tuning decreases the response time and increases the speed for detecting the presence of particular chemical agents at the remote location.

Figure 1:
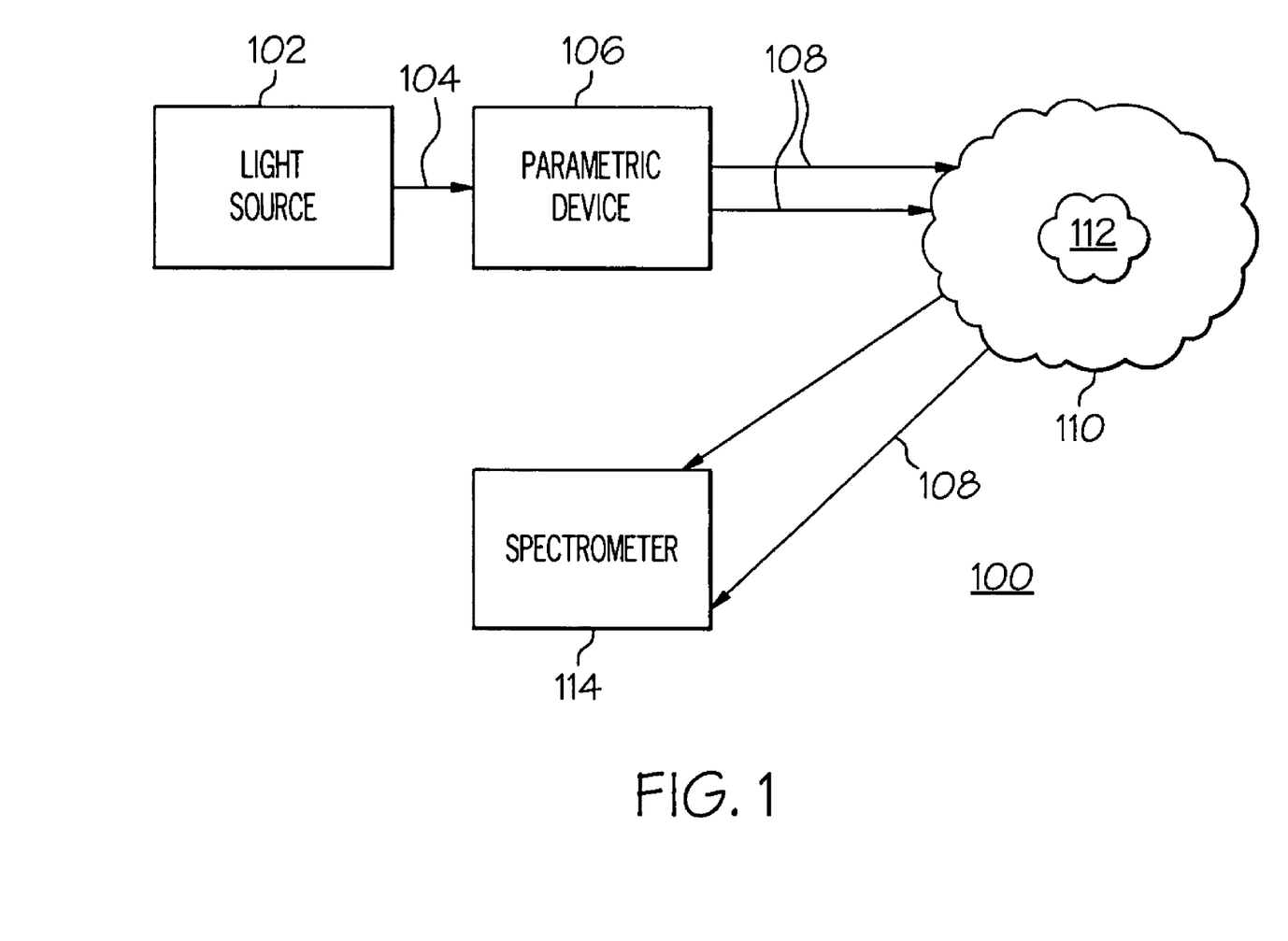
FIG. 1 is a simplified diagram that shows parts of a flash spectroscopy system for standoff chemical detection.

With reference to the drawings, embodiments of flash spectroscopy for use in chemical identification and detection will now be described. FIG. 1 shows parts of a flash spectroscopy system 100 for standoff chemical detection. A light source 102 produces a pump wave 104, for example in the infrared region, that is incident on a nonlinear crystal or crystalline material that is used as a parametric device 106. The parametric device 106 may be configured as a parametric amplifier (OPA), a parametric generator (OPG) or a parametric oscillator (OPO).

The parametric device 106 may be used in conjunction with one or more pump waves to generate light through parametric interaction or generation. Parametric interaction or generation involves the mixing or exchange of energy among three optical waves or fields, i.e., pump, signal, and idler waves, within a nonlinear crystal. For parametric interaction to occur within a nonlinear material or crystal, the energy of the three interacting waves is conserved. Momentum or phase is also conserved, although a small amount of mismatch will still allow for energy transfer among the three waves within the nonlinear crystal. Through parametric generation one or two of the three optical waves can be selectively amplified by converting energy from the other optical waves.

The conservation of momentum requirement, including the small range of allowable mismatch, is referred to as the "phase matching" condition. The larger the mismatch in momentum or phase, the less efficient the three-wave or parametric interaction will be. Because nonlinear crystals are birefringent, such crystals support two or more modes of phase velocities and consequently have two or more indices of refraction, i.e., the ordinary and extraordinary, depending upon the orientation of wave travel and polarization within the crystals. For a given nonlinear crystal, the indices of refraction determine which set of wavelengths satisfy the phase matching condition.

Nonlinear materials or crystals used for the parametric device 106 may be characterized according to how the effect of double refraction or birefringence affects incident light once it enters the particular crystal. A nonlinear crystal may be referred to as a Type I or a Type II crystal. A nonlinear crystal is referred to as a Type I crystal when an incident or "pump" wave is doubly refracted into signal and idler fields or waves that have the same polarization, which is orthogonal to the pump wave. A Type II parametric crystal is one producing orthogonally polarized signal and idler waves from a pump wave. The parametric device 106 may be configured in either Type I or Type II configuration.

The parametric device 106 may be tuned or configured at or near its degeneracy point. The degeneracy point of a nonlinear crystal is the point at which the two non-pump waves, known as the signal and idler waves, each have the same frequency or energy, which is one-half that of the pump wave. The region near to the degeneracy point, where the signal and idler waves are nearly equal in energy or frequency, may be referred to as a degeneracy region. The pump wave 104 may be selected or tuned based on the degeneracy point of the parametric device 106.

The degeneracy point and phase matching conditions of the particular nonlinear crystalline material used in the parametric device 106 may be determined from dispersion relations known as Sellmeier equations. Sellmeier equations are mathematical models of measured refraction and polarization conditions that are consistent with the permittivity and impermeability tensors of the particular nonlinear crystalline material, e.g., the polarizations and directions of modes that are consistent with the index ellipsoid for the material. Refractive index measurements of a material at various temperatures and wavelengths may be used to derive the Sellmeier equation(s) for that material.

Sellmeier equations generally express the fact that typical solids have several electron states with different resonance frequencies contributing to the dielectric constant of the solid. Sellmeier equations may be of the following or similar form:

$$n^2 = A + [B/(1-(C/\lambda)^2)] - D\lambda^2, \quad (1)$$

where n is the index of refraction, either ordinary or extraordinary, of a particular nonlinear crystal, and A, B, C, and D, are known as the Sellmeier coefficients. The Sellmeier coefficients and the index of refraction may be determined for coordinates axes, e.g., principal or x, y, and z-axes, of a particular crystal material. Other forms of the Sellmeier equations are known and these may take into account the temperature of the nonlinear crystal.

Tuning of the parametric device 106 may be performed by adjusting its orientation or "angle tuning," for example on a prism table or equivalent, by adjusting the wavelength of the pump wave, by controlling the temperature of the parametric device, i.e., "temperature tuning," or any combination of the preceding. When appropriate, the temperature of the parametric device 106 may be controlled. For example, the parametric device 106 may be cooled in a nitrogen Dewar or heated in an oven.

With continued reference to FIG. 1, the parametric device 106 converts the pump wave 104 to a broadband output 108 by three-wave mixing or parametric interaction. The broadband output 108 may include a signal wave and an idler wave that may be equal, substantially equal, and/or overlap in wavelength value due to the configuration of the parametric device 106 at or near the degeneracy point or region. The broadband output 108 is directed, for example by transmission optics, to a remote location 110 that is located at a distance, referred to as the "standoff distance," away from the parametric device 106.

For a given parametric device, e.g. 106, the magnitude of the bandwidth of the broadband output 108 at or near the degeneracy point or region may be computed by the following equation:

$$\Delta k = [(\partial k_s/\partial \omega_s) - (\partial k_i/\partial \omega_i)]\Delta\omega + [(\partial^2 k_s/\partial \omega_s^2) - (\partial^2 k_i/\partial \omega_i^2)]\Delta\omega^2/2; \quad (2)$$

where each first derivative is the group velocity of a respective wave, $\Delta k$ is the momentum or phase mismatch and which may be set to $2\pi/L$ where L is the crystal length of the parametric device, the subscripts $_s$ and $_i$ refer to the signal and idler waves, respectively, and $\Delta\omega$ is the magnitude of parametric device bandwidth at or near the degeneracy point. Equation 2 shows that the bandwidth $\Delta\omega$ of the signal or idler waves depends on the group velocity difference. Because the group velocity difference becomes infinite at the degeneracy point, $\omega_i = \omega_s$, a second-order term in bandwidth representing the velocity dispersion is introduced as indicated.

Equation 2 simplifies the calculation of the expected spectral range for a parametric device of a particular material by ignoring temperature and angular variations. Use of Eq. 2 may facilitate selection of the material of the parametric device to produce a broadband output of sufficient bandwidth to detect particular chemical agents in or near real time without the need for tuning a light source. Bandwidth may be expressed in terms of full-width half-maximum value or 3 dB value, in terms of 1/e value, or in terms of the ratio of the square of the total average intensity divided by the integral of the square of the power spectral density.

Suitable mathematical software such as MATHCAD, MATLAB and MATHEMATICA may facilitate the solution of Eq. 2 to determine the spectral range of the broadband output of the parametric device for a given nonlinear material. Such software may also facilitate the solution of Sellmeier equation(s) to find desired variables or to determine coefficients for a particular nonlinear crystal. MATHCAD is a registered trademark for a computer program registered to Mathsoft, Inc. of One Kendall Square, Cambridge Mass. 02139. MATHEMATICA is a registered trademark for a computer program registered to Wolfram Research, Inc. of 100 Trade Center Drive, Champaign, Ill. 61820. MATLAB is a registered trademark for a computer program registered to The MathWorks, Inc. of 3 Apple Hill Drive, Natick, Mass. 01760.

Referring again to FIG. 1, various wavelengths of the broadband output 108 may be absorbed at the remote location 110 by any chemical agents 112 that are present. Such chemical agents 112 may be any chemical or biological material. For example, they may include organophosphates and may include chemical warfare agents in any form such as solids, liquids, gases, and aerosols. Chemical agents may also include any of the following: biotoxins, blister agents/vesicants, blood agents, caustics or acids, choking or pulmonary agents, incapacitating agents, metals, nerve agents, organic solvents, riot control agents including tear gas, pesticides, toxic alcohols, and vomiting agents. After interacting with the chemical agents 112 at the remote location 110, the broadband output 108, including any attenuation of frequencies due to absorption by chemical agents, may be detected and measured by a spectrometer 114 or spectrophotometer.

The spectrometer 114 functions to (1) receive the broadband output from the remote location 110, (2) disperse the broadband output 108 into sub-bands or channels, and (3) detect the intensities of the dispersed sub-bands or channels. The spectrometer 114 may be a single device, e.g., integrated, or a collection of devices or discrete optical and electrical components. The spectrometer 114 may also multiplex the intensity signals, producing an absorption spectrum over a portion of the spectral range of the spectrometer 114. The operational parameters of the spectrometer 114, e.g., spectral range, spectral bandwidth of the sub-bands, spectral sampling, and detectivity, may be selected or designed by taking into consideration various factors such as the stand-off distance, the power of the light source 102, the degree of coherence of the broadband output 108, and features of the absorption spectra of the chemical agents of interest.

The intensity signals of the channels may also be multiplexed at a location separate from the spectrometer 114, i.e., a computer or optical multispectrum analyzer (OMA). Once an absorption spectrum has been produced, a comparison may be made with the known absorption spectra of various chemical agents. The spectrometer 114 may make such a comparison or suitable devices that are separate from the spectrometer 114 may perform the comparison. For example, a suitable computer or optical multispectrum analyzer (OMA) may be used for the comparison.

Regarding the light source 102, any suitable coherent or quasi-coherent light source may be used. Examples include, but are not limited to, lasers or other non-thermal light sources. Suitable lasers may have gas, liquid dye, diode, or solid-state active media. The light source 102 may include a laser producing an output that is converted to a desired pump wavelength by a nonlinear optical device including a parametric device. The pump wave 104 produced by the light source 102 may be filtered for example by a Fabry-Perot etalon or other filtering device. Furthermore, a tunable light source 102 may be used so that the pump wave is tunable across a range.

Figure 2:
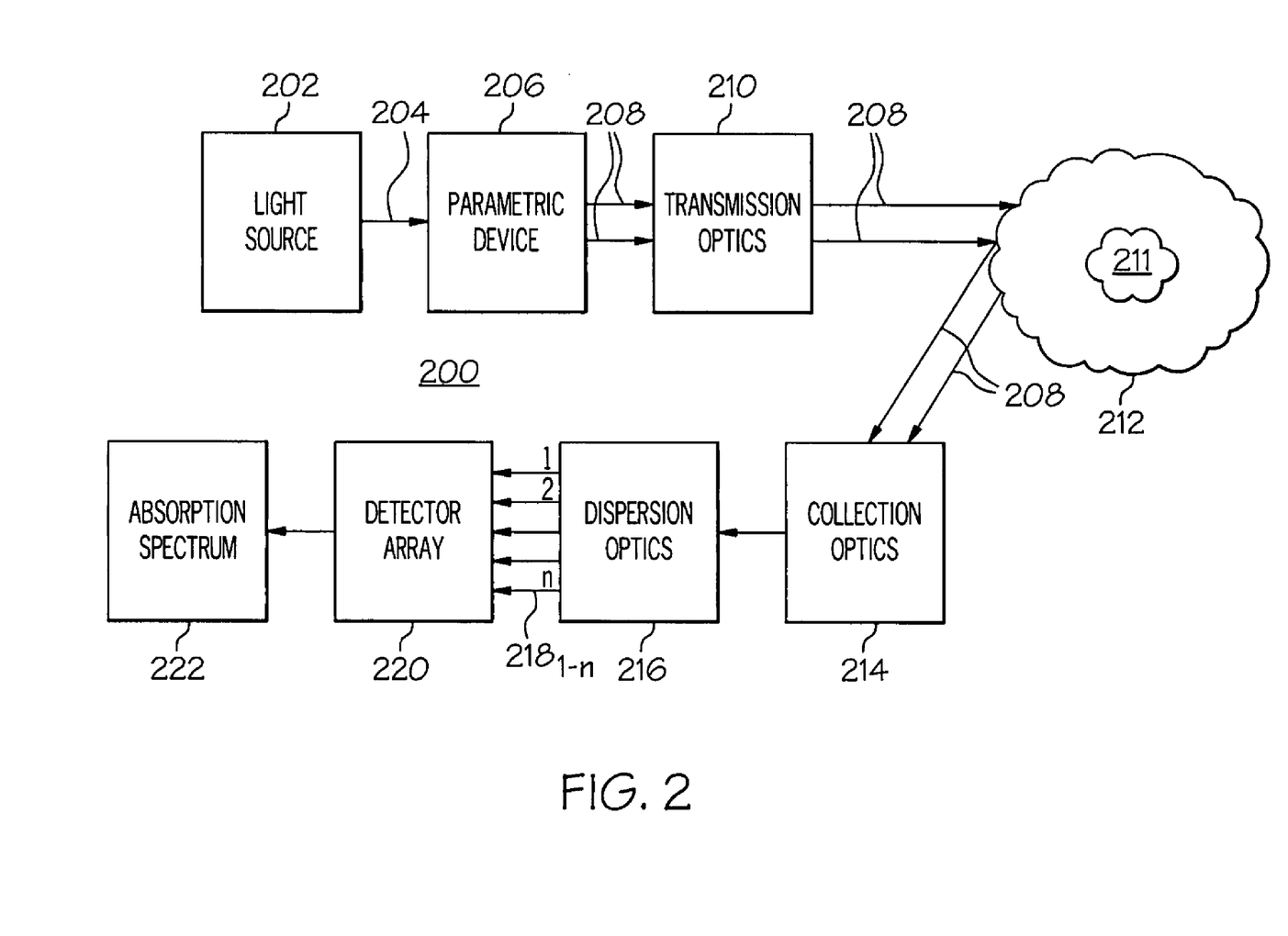
FIG. 2 is a simplified block diagram of a different embodiment of a flash spectroscopy system.

Referring now to FIG. 2, another embodiment of a flash spectroscopy system 200 is shown. A light source 202, e.g., a laser, produces a pump wave 204 that is sent to a parametric device configured at a degeneracy point or region 206. The light source 202 may also include transmission optics. The parametric device 206 produces a broadband output 208. By appropriate selection of the light source 202 and of the nonlinear material or crystal of the parametric device 206, the broadband output 208 may include a desired region of the optical spectrum, e.g., ultraviolet, visible, or infrared.

Transmission optics 210 may receive the broadband output 208 and direct the broadband output 208 to chemical agents 211 at a remote area 212. The transmission optics 210 may include suitable lenses to expand and collimate the broadband output 208. Lenses of the transmission optics 208 may be configured in a telescope or beam expander configuration. After interaction with any chemical agents 211 that are present, the broadband output 208 may be received from the remote area 212 by collection optics 214, which may include suitable lenses, filters, and apertures.

The collection optics 214 may send the broadband output 208 to dispersion optics 216 for dispersion into channels or sub-bands $218_{1-n}$. Detectors or pixels in a detector array 220 detect the intensities of the sub-bands $218_{1-n}$. The dispersion element or optics 216 may be any suitable kind. Examples include but are not limited to diffraction gratings, prisms, electro-optic elements such as a self-focusing elements, Hadamard masks, or the like.

The detector array 220 may multiplex or combine the intensities of the sub-bands $218_{1-n}$ to produce an absorption spectrum 222. The presence of certain chemical or biological agents may then be determined through comparison of the absorption spectrum 222 to known absorption spectra of chemical agents of interest. The comparison may be accomplished by suitable techniques including but not limited to use of a matched filter or filters corresponding to known absorption spectra or other known techniques. The comparison may be performed by signal processing hardware or software, or both, which may be included, for example, in a spectrometer or in a computer.

Any suitable detector array 220 may be used for the signal detection of the sub-bands $218_{1-n}$ dispersed from the broadband output 208. For example, a detector array may include but is not limited to quantum well infrared photodetectors (QWIPs), photodiodes, charged coupled devices (CCDs), avalanches photodiodes, bolometers including microbolometers, and phototransistors. The detector array may be one-dimensional or two-dimensional. The detector array may be a focal plane array (FPA), placed in the focal plane of dispersion optics of the system. The signals from parallel detector elements of two-dimensional arrays may be added to improve the signal-to-noise ratio and thereby improve detection of the absorption spectrum. For any type of detector used, the detector material(s) may be matched to the spectral range of the broadband output 208. The detector may be cooled by appropriate methods, e.g., by a Dewar, to facilitate detection of the sub-bands $218_{1-n}$.

Use of a flash spectroscopy system for remote chemical detection at a standoff distance will now be described with reference to FIG. 2. Light source 202 generates a pump wave 204, which is incident on a parametric device 206, e.g., a parametric generator that is configured at or near its degeneracy point. A broadband output 208 is produced by the parametric device 206 and travels through transmission optics 210, which may include two lenses in a telescope or beam-expander configuration. The broadband output 208 is then directed to a remote location 212 to determine the presence of chemical agents 211. The broadband output 208 interacts with any chemical agents 211 that are present at the remote location 212 and those chemical agents 211 that are present absorb characteristics wavelengths of light of the broadband output 208.

The broadband output 208 is reflected or back-scattered to collection optics 214, which may include one or more focusing lenses. The broadband output 208 is then dispersed by dispersion optics 216, e.g., a grating, into sub-bands $218_{1-n}$, which are detected by detector array 220. The detector array 220 multiplexes the intensities of the sub-bands $218_{1-n}$ and produces an absorption spectrum 222. The absorption spectrum 222 may then be compared to a library of known absorption spectra, which may include but are not limited to nerve gas and blister agent IR absorption spectra.

The remote location 212 is located at a standoff distance, which may be influenced and adjusted according to geographical constraints, the available optical power of the light source, the signal-to-noise ratio (S/N) parameters of the spectrometer including the detectivity of the detectors of the detector array 220, and the signal-to-noise ratio of features within the detected absorption spectrum 222.

Figure 3:
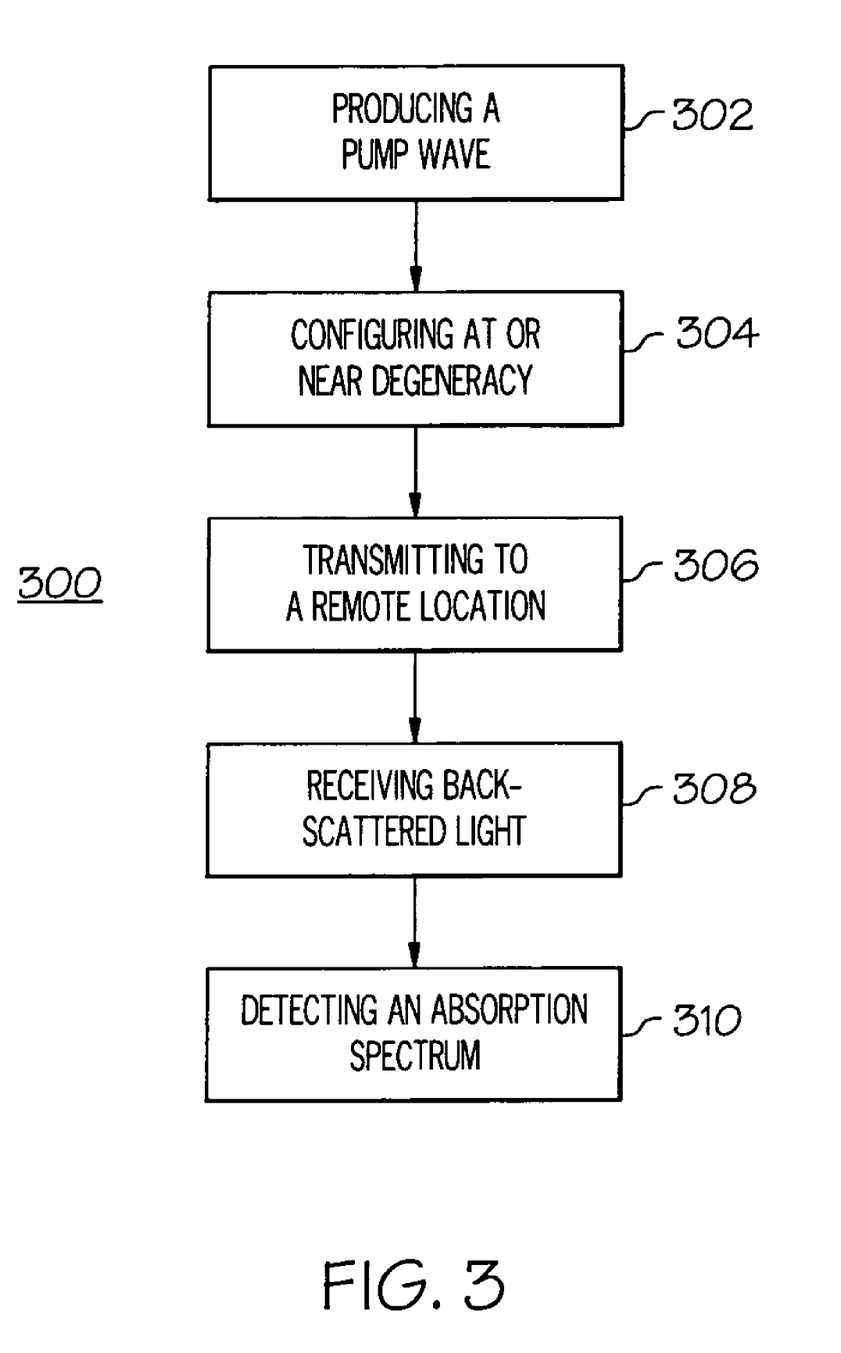
FIG. 3 is a flow chart of a method of detecting chemical agents at a remote location using flash spectroscopy.

With reference now to FIG. 3, a flow chart is shown for a method of detecting chemical agents at a remote location using flash spectroscopy 300. A pump wave is produced 302 by an appropriate light source, and this pump wave is incident on a parametric device that is configured at or near a degeneracy point 304. A broadband output, for example in the IR region, is transmitted from the parametric device to a remote location 306, where one or more chemical agents are present that may absorb portions of the broadband output. A portion of the broadband output, which may be backscattered light, is received 308 from the remote location, and an absorption spectrum is detected 310.

Figure 4:
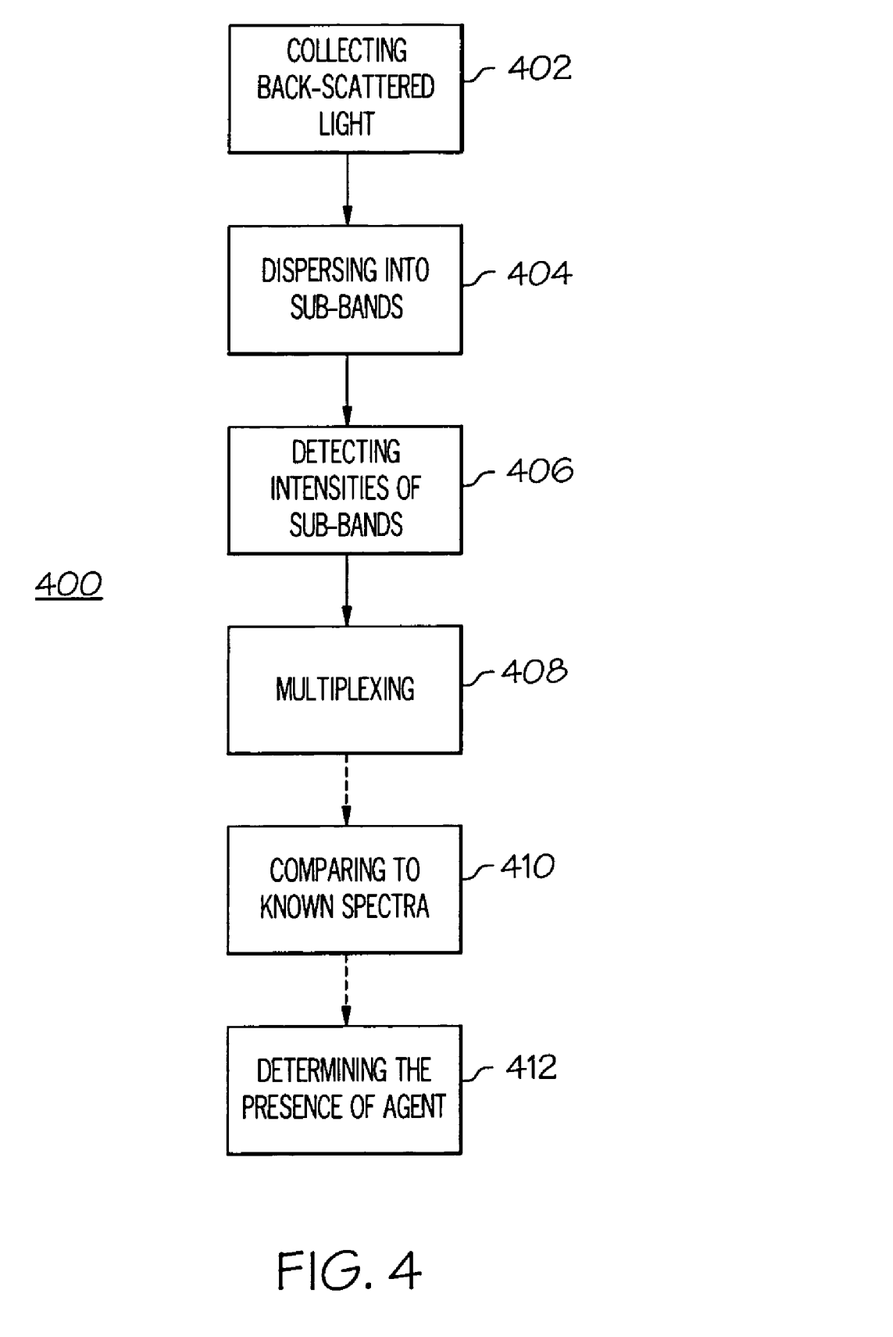
FIG. 4 is a flow chart of additional steps in the method of FIG. 3.

FIG. 4 is a flow chart of a method 400 of additional steps in the receiving 308 and detecting 310 steps of method 300. That portion of the broadband output that is received from the remote location may be collected 402 by collection optics and then dispersed 404 into a number of sub-bands or channels. The intensities of the sub-bands are detected 406 and then multiplexed or combined to form an absorption spectrum 408. The absorption spectrum may then be compared or correlated 410 to known chemical absorption spectra to determine 412 the presence of one or more chemical agents at the remote location.

The parametric device used for the present invention may be configured as an optical parametric amplifier (OPA), an optical parametric generator (OPG), or an optical parametric oscillator (OPO). In certain embodiments, a parametric generator (OPG) may be used because of the tendency for such devices to produce gain broadening when compared to OPOs. When an OPG is used, single-pass or multiple pass configurations may be employed. OPOs may be used but gain narrowing may occur during the multiple passes within the resonator of the device.

Factors that may be considered in the selection of the material for the parametric device may include, but are not limited to, individually or severally the nonlinear optical coefficient, nonlinear amplification or gain threshold, the laser or optical damage threshold, spectral transmission range, acceptance angle, walk off angle, and the bandwidth at the degeneracy point. Other factors may be considered such as the nonlinear figure of merit, which is defined as $d^2/n^3$, where $d=d_{NL}$ and is the nonlinear optical coefficient and n is the average refractive index near the center of transparency of the particular material.

Without limiting the generality of the previous description, suitable materials or crystals for the parametric device, e.g., 106, may include, but are not limited to, any of the following: ammonium diphosphate ($NH_4H_2PO_4$ or "ADP"), beta (β) barium borate (BBO), gallium selenide (GaSe), barium lithium niobate ($Ba_2LiNb_5O_{15}$), cadmium gallium sulfide ($CdGa_2S_4$), cadmium selenide (CdSe), cadmium germanium diarsenide ($CdGeAs_2$), lithium niobate ($LiNbO_3$), stoichiometric lithium niobate ($LiNbO_3$), lithium tantalate ($LiTaO_3$), lithium triborate ($LiB_3O_5$ or "LBO"), potassium diphosphate ($KH_2PO_4$ or "KDP"), potassium titanyl phosphate ($KTiOPO_4$ or "KTP"), potassium titanyl arsenate ($KTiOAsO_4$ or "KTA"), indium doped potassium titanyl arsenate ($In:KtiOAsO_4$ or "In:KTA"), rubidium titanyl arsenate $RbTiOAsO_4$ (RTA), silver gallium selenide ($AgGaS_2$), silver gallium sulfide ($AgGaS_2$), silver arsenic sulfide ($Ag_3AsS_3$ or "proustite"), potassium niobate ($KnbO_3$), neodymium doped magnesium lithium niobate ($Nd:MgLiNbO_3$), and suitable chalcopyrites. Suitable nonlinear materials may be chosen from the following compound systems or alloys: $(Zn_{1-x}Cd_x)GeAs_2$, $Zn(Ge_{1-x}Si_x)As_2$, and $Zn(Ge_{1-x}Si_x)P_2$. For these compound systems, the associated second-order nonlinear susceptibility, and hence nonlinear coefficient, may increase correspondingly with the substitution of As for P, Ge for Si, and Cd for Zn. Other suitable nonlinear materials may be selected from the following compound systems or alloys: $AgGa_{1-x}In_xSe_2$ and $CdGe(As_{1-x}P_x)_2$.

In addition to the materials described above, quasi phase matching (QPM) or periodically-poled materials may be used for the parametric device. Such QPM materials utilize periodic domain inversion, or periodic poling, and can be used to form a QPM grating that compensates for phase velocity mismatch between the interacting waves or signals. A change in the sign of the nonlinear coefficient accompanies the domain reversal and consequently such gratings can compensate for dispersion due to the refractive index of the material.

Quasi-phase matching (QPM) permits phase-matched operation at many wavelengths. The period of the modulation, or grating, can be designed to provide phase matching of any frequency conversion process so that the nonlinear crystal properties can be precisely tailored to desired requirements. In addition, such gratings need not be truly periodic. For example, chirped gratings can be used where the length of each domain with respect to a preceding one, is adjusted in length or "chirped." Chirped grating may be used to enhance properties such as the acceptance bandwidth and to decrease walk-off and facilitate temporal pulse compression.

Periodically-poled materials utilizing QPM may allow for a combination of propagation direction and polarizations to be selected that exploit the largest nonlinear coefficient in a particular nonlinear crystal. Suitable periodically poled materials for the parametric device may include, but are not limited to, periodically twinned gallium arsenide (PTGaAs) and other lithography-patterned materials, periodically poled lithium niobate (PPLN), periodically poled KTP (PP-KTP), periodically poled RTA (PPRTA). Aperiodically poled materials including but not limited to aperiodically poled lithium niobate (APPLN) may be used for the parametric device. Bandwidth-limiting effects such as temporal walk off, restricted acceptance bandwidth and back conversion may be avoided by suitably designed crystal with a linearly chirped grating period.

Materials with large nonlinear coefficients and figures of merit may provide sufficient nonlinear gain for the parametric device so that OPO configurations are not required. Guided-wave QPM materials, in which a QPM material is incorporated into a guided-wave structure such as an annealed-proton-exchanged $LiNbO_3$ structure, may also be used. In certain embodiments, guided-wave QPM parametric materials may be used in the parametric device to decrease diffraction effects and increase available parametric gain.

The degeneracy point for a particular nonlinear crystal used as a parametric device may be (1) known a priori, (2) determined from appropriate Sellmeier equations, (3) determined from known tuning curves, (4) determined from derived tuning curves, and/or (5) determined from an appropriate index ellipsoid. A suitable temperature for temperature tuning may be determined from the temperature-dependent Sellmeier equation for the particular crystal material.

Accordingly, it should be understood that an absorption spectrum of particular chemical agents at a remote location can be determined in real time or near real time through use of the present invention. For example, the infrared (IR) absorption spectra of many major chemical warfare agents including nerve agents such as VX, Sarin, Cyclosarin, Soman, Tabun, as well as blister agents such as mustard gas, have been observed and characterized. At least eight major chemical agents have IR absorption bands clustered around nine microns. These include Tabun (NATO designation "GA"), Sarin (GB), Soman (GD), VX, distilled mustard gas (HD), chloroacetophenome (CN), o-chloro-benzylmalononitrile (CS), and BZ. See for example, "Atlas of Infrared Spectra (8–13 micron) of Chemical Agents and Potential Interferences," U.S. Army Chemical Systems Laboratory (1977), the contents of which are incorporated by reference herein. Chemical agents such as these may be determined to be a remote location by comparing a detected absorption spectrum to a library or database of known absorption spectra.

In certain embodiments, a parametric device may be used that produces a broadband output having bandwidth of greater than 200 wave numbers per centimeter (200 $cm^{-1}$), using conventional definitions of bandwidth. In exemplary embodiments, a parametric device may be used that produces a broadband output having a bandwidth of greater than 300 wave numbers per centimeter (300 $cm^{-1}$).

In certain embodiments, a light source may be used that produces an infrared pump wave of between 4 and 5 microns in wavelength, and preferably near 4.5 microns. With a pump wave in such a range, a parametric device with a transmission range from four microns to 12 microns that is configured at its degeneracy point produces a broadband output in the 8 to 12 micron range. A broadband output with this spectral range may be used to detect organophosporous or organophosphate compounds, including nerve, blister, and debilitation agents. Most nerve agents are organophosphate ester derivatives of phosphoric acid and have absorption spectra with high signal-to-noise ratio features in the 8 to 12 micron range. This spectral range may also be used to detect phosphorous group(s) in other chemical agents. Methylphosphonic acid (MPA), which is formed by the hydrolysis of Sarin or Soman and is more stable than either, may also be detected by absorption spectra features in the 8 to 12 micron range.

Figure 5:
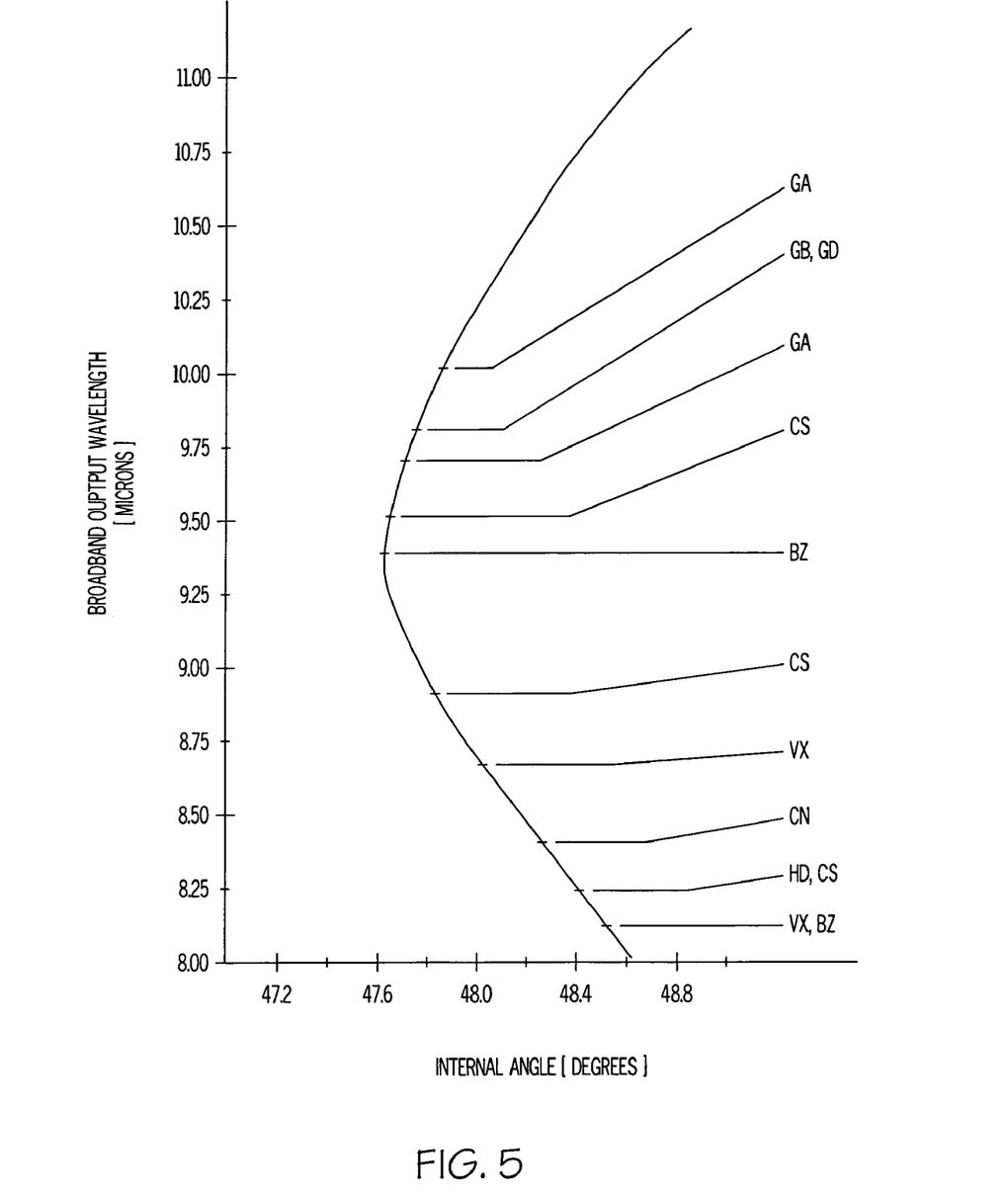
FIG. 5 is graph of a broadband output with wavelength calculated versus internal angle for AgGaSe$_2$.

In certain embodiments, carbon monoxide (CO) or quantum cascade (QC) lasers may be used as the light source to produce a pump wave near 4.5 microns so that the parametric device produces a broadband output including the nine-micron region. As shown in FIG. 5, various chemical agents including certain well-known deadly nerve gases have unique absorption spectra details in the nine-micron region of the infrared spectrum. Quantum cascade (QC) lasers may be used in certain embodiments to obtain compact sources of desired infrared radiation since such QC lasers may be fabricated at any wavelength from approximately 4.5 to 17 microns using AlInAs/InGaAs lattices on indium phosphide (InP).

According to the present invention, a chemical absorption spectrum indicating the presence of one or more chemical agents at a remote location may be produced with pulsed laser light source with only one or a few pulses. Moreover, operational parameters such as the power of the light source may be adjusted to extend the stand-off distance to the remote location so that in the case of poisonous or deadly chemical agents, these agents may be detected with a reduced risk to human life.

The effective stand-off distance may be influenced by a particular transmission window, the chemical agents of interest, the detectivity of the detector array, the wavelength spread of the broadband output, geographical constraints, the available optical power of the light source, and the signal to noise ratio parameter of the spectrometer.

By searching for high signal-to-noise ratio features that are within certain transmission windows, and by the appropriate selection of high power light sources and high detectivity detectors, stand off distances of hundreds of meters to many kilometers may be realized. Such distances make the use of the present invention ideal for chemical agent detection within a city or urban environment. The present invention is also well suited for use in place of the Joint Service Lightweight Standoff Chemical Agent Detector (JSLSCAD) because of the illumination provided by the light source and speed with which chemical agents may be detected.

The following examples are presented to show the broad scope and applicability of the present invention.

EXAMPLE 1

For this prospective example, a CO laser is used as a light source and $AgGaSe_2$ or $CdGeAs_2$ is used for the material of a parametric device. Such a carbon monoxide (CO) laser can produce many laser lines from about 4.8 and to about 8.3 microns and can be line tuned to select specific lines. In this example, a CO laser is used as a light source and may produce a pulsed output, with the pulse wavelengths centered at 4.8 microns. This prospective example demonstrates how a suitable light source producing light near 4.8 microns can be used to pump a parametric device made from a suitable nonlinear crystal such as $AgGaSe_2$ or $CdGeAs_2$ to produce a broadband output over the range of 8.6 to 10.6 microns for use to detect chemical warfare agents.

The pulse characteristics may be actively controlled by known timing and/or compression techniques and devices. The output from the CO laser have sufficient fluence and are used as a pump wave and sent to a parametric device, e.g., OPG, made of $AgGaSe_2$ or $CdGeAs_2$. The parametric device is configured at its degeneracy point or region. The parametric device degenerately amplifies the CO laser output and produces a broadband output that includes signal and idler waves that are nearly equal. As a result of the degeneracy configuration, the broadband output is centered at about 9.6 microns. The broadband output may include a bandwidth or linewidth, e.g., FWHM, 3 dB, or 1/e, of plus or minus ten percent, or more, of the pump wavelength, corresponding to a range of approximately 8.6 to 10.6 microns. Such a broadband output is in the spectral range where the absorption spectra of many chemical warfare agents have high signal-to-noise ratio features.

With reference to FIG. 5, a graph is shown indicating high signal-to-noise-ratio features of certain well-known nerve agents with respect to the broadband output of Example 1. The axes shown are wavelength versus the internal angle for $AgGaSe_2$, where the internal angle refers to how the crystal is cut relative to the inherent crystal or principal axes including the optic axis. The wavelength of the pump wave is 4.635 microns and the broadband output starts near 8 microns and extends to about 10.2 microns.

The pump wavelength indicated in FIG. 5 was calculated based on a carbon dioxide ($CO_2$) laser line R(20), corresponding to the transition of the rotational quantum number from j=20, the most populous or strongest line for $CO_2$, to j=21. A CO laser operating near 4.5 microns may produce a similar broadband output for such a parametric device. The positions of absorption spectra peaks for various chemical agents are indicated. For example, VX is shown with an absorption peak at approximately 8.63 microns. The absorption peaks of other chemical agents are disclosed in "Atlas of Infrared Spectra (8–13 micron) of Chemical Agents and Potential Interferences," U.S. Army Chemical Systems Laboratory (1977), the contents of which are incorporated by reference herein.

The broadband output from the parametric device may be directed to a remote area containing a chemical agent, such as VX, Sarin, or Soman gas or others, where the chemical agent absorbs various components of the broadband output. A portion of the broadband output is reflected or backscattered to the vicinity of a spectrometer that includes dispersion optics and a detector. The backscattered light of the broadband output is dispersed by dispersion optics, e.g., a diffraction grating, which disperses the back-scattered light into sub-bands.

The detector may include a one-dimensional (1D) array made of detector elements or pixels. For the detector of Example 1, the pixels may be made of suitable materials to wavelengths over the 8 to 10.5 micron range. The individual elements of the detector array detect the intensity of each sub band. The individual detectors may be made of different materials to detect a limited range of wavelengths corresponding to an individual sub-band. The detector array may also include a two-dimensional (2D) focal plane array, for example, an array of vanadium oxide ($VO_2$) microbolometers. The detector multiplexes the intensities to produce a detected absorption spectrum over the span of the broadband output. The detected absorption spectrum may then be compared to those of known chemical or biological agents to determine if one or more are present at the remote location.

EXAMPLE 2

A two-step wavelength conversion process was used to pump a Type I $AgGaSe_2$ OPO. The light source included a laser and an OPO, i.e., a 1.06 micron Nd:YAG laser that was used pumped a Type II KTP OPO. A four-micron coherent broadband output was produced. The pump laser was a Continuum Model NY61 YAG laser. The output of the Nd:YAG pump laser was used as a 1.06 micron pump wave for the Type II KTP OPO cut with an internal angle of θ=53.5 degrees. The pump wave was converted by the Type II KTP OPO to a 1.99/2.28 micron signal/idler pair.

The shorter signal wavelength, i.e., 1.99 micron, was used to pump a Type I phase-matched OPO from Cleveland Crystals containing a 10×10×40 mm anti-reflection (AR) coated silver gallium selenide ($AgGaSe_2$) crystal cut with an internal angle of θ=49 degrees. The Type I parametric device was configured near its degeneracy point and generated an infrared broadband output that was centered around 4 microns.

The broadband output was directed to a gas cell containing nitrous oxide ($N_2O$) at 380 torr. Light that was backscattered from the gas cell was collected by a prism spectrometer having a multiplexed 2D pyroelectric array. The spectrometer was a Spiricon Model Pyrocam Pyroelectric (128×128). Pixels in the vertical direction of the 2D array were summed, and the results from five pump pulses were averaged. The signals from the multiplexed array were combined and an absorption spectrum was produced that had a range from approximately 3.75 to 4.25 microns. This absorption spectrum was compared with and fit to a known chemical absorption spectrum of nitrous oxide with a high degree of correlation, though it is believed by the inventors that the resolution of the detector array could have been improved. The entire process was accomplished in approximately 0.1667 seconds (⅙ s).

Although the present invention has been described in detail with reference to certain versions thereof, other versions are possible. For example, while the previous description has generally been directed to the identification of chemical agents by use of an infrared broadband output, one or skill in the art should understand that use and production of ultraviolet and visible light broadband outputs are within the scope of the present invention.

While the description of embodiments of the present invention has been generally directed to the detection of back-scattered light in a monostatic configuration, where the light source or transmitter and the spectrometer or receiver are in the same location, the scope of present invention includes other configurations. For example, bistatic configurations, where the light source or transmitter and the spectrometer or receiver are at different locations, may be utilized. Such bistatic configurations may include the use of detectors placed near 180 degrees from the light source or parametric device and substantially collinear with the remote location. Furthermore, more than one detector or detector array may be used and these may be placed at different locations. Additionally, while the light sources have been generally been described as lasers or non-thermal light sources, suitable sources may also include frequency-shifted outputs from such sources.

Those skilled in the art will understand that the present invention can be varied in many ways as will be apparent from the above description. The invention should therefore only be limited insofar as is required by the scope of the following claims.

The reader's attention is directed to all papers and documents that are filed concurrently with this specification and which are open to public inspection with this specification, and the contents of all such papers and documents are incorporated herein by reference. All the features disclosed in this specification, including any accompanying claims, abstract, and drawings, may be replaced by alternative features serving the same, equivalent or similar purpose, unless expressly stated otherwise. Thus, unless expressly stated otherwise, each feature disclosed is one example only of a generic series of equivalents or similar features. Any element in a claim that does not explicitly state "means for" performing a specific function, is not to be interpreted as "means" or "step" clause as specified in 35 U.S.C. § 112, paragraph 6.

What is claimed is:

1. A flash spectroscopy standoff chemical detection system comprising:
   a light source;
   a parametric device configured to receive a pump wave from said light source at a degeneracy point of said parametric device;
   a broadband output produced by said parametric device, wherein said broadband output is transmitted to a remote location and wherein said broadband output has a bandwidth or linewidth with a full-width half-maximum value of about 5 percent to about 25 percent of a central broadband output wavelength; and
   a spectrometer operable to receive said broadband output from said remote location and to produce an absorption spectrum.

2. The system of claim 1, wherein said broadband output comprises an idler wave and a signal wave.

3. The system of claim 2, wherein said idler wave is substantially equal to said signal wave.

4. The system of claim 1, wherein said broadband output has a bandwidth or linewidth with a full-width half-maximum value of about 10 percent to about 20 percent of a central broadband output wavelength.

5. The system of claim 1, wherein said broadband output has a bandwidth or linewidth with a full-width half-maximum value of greater than 200 $cm^{-1}$.

6. The system of claim 1, wherein said broadband output has a bandwidth or linewidth with a full-width half-maximum value of greater than 300 $cm^{-1}$.

7. The system of claim 4, wherein said pump wave has a central wavelength equal to about one-half of said central broadband output wavelength.

8. The system of claim 2, wherein a central wavelength of one of said idler wave and said signal wave is between about 8 microns to about 12 microns.

9. The system of claim 2, wherein a central wavelength of one of said idler wave and said signal wave is between about 3 microns to about 5 microns.

10. The system of claim 1, wherein said spectrometer comprises an optical dispersion element configured to receive said broadband output and to disperse said broadband output into a plurality of sub-bands after said broadband output has been received from said remote location.

11. The system of claim 10, wherein said spectrometer comprises a detector array configured to receive said sub-bands, said detector array operable to produce a multiplexed absorption spectrum from said sub-bands.

12. The system of claim 11, wherein said detector array comprises a 1D array.

13. The system of claim 12, wherein said detector array comprises 128 detector elements.

14. The system of claim 12, wherein said detector array comprises 256 detector elements.

15. The system of claim 11, wherein said detector array comprises a 2D array.

16. The system of claim 15, wherein said detector elements are configured in a 128 by 128 configuration.

17. The system of claim 11, further comprising a matched filter corresponding to a known chemical agent.

18. The system of claim 1, wherein said pump wave has a wavelength between about four microns to about five microns.

19. The system of claim 1, wherein said parametric device comprises collimating or transmission optics.

20. The system of claim 1, wherein said parametric device comprises an optical parametric generator.

21. The system of claim 1, wherein said parametric device comprises an optical parametric oscillator.

22. The system of claim 1, wherein said light source comprises a carbon monoxide or carbon dioxide gas laser.

23. The system of claim 1, wherein said light source comprises a diode laser.

24. The system of claim 23, wherein said light source comprises a quantum cascade diode laser producing a pump wave having a 4.5-micron wavelength.

25. The system of claim 23, wherein said light source comprises an AlInAs/InGaAs quantum cascade diode laser.

26. The system of claim 1, wherein said parametric device is configured in a Type I configuration.

27. The system of claim 1, wherein said parametric device is configured in a Type II configuration.

28. The system of claim 1, wherein said parametric device is made of cadmium germanium arsenide ($CdGeAs_2$).

29. The system of claim 1, wherein said parametric device is made of silver gallium selenide ($AgGaSe_2$).

30. The system of claim 1, wherein said parametric device is made of periodically twinned gallium arsenide (PTGaAs).

31. The system of claim 11, wherein said detector array comprises a quantum well infrared photodetector (QWIP).

32. A method of standoff chemical detection comprising the steps of:
    supplying a pump wave to a parametric device configured at a degeneracy point;
    producing a broadband output, wherein said broadband output has a bandwidth or linewidth with a full-width half-maximum value of about 5 percent to about 25 percent of a central broadband output wavelength;
    directing said broadband output to a remote location containing a chemical agent;
    detecting said broadband output from said remote location; and
    producing a chemical absorption spectrum of said chemical agent.

33. The method of claim 32, wherein said step of detecting further comprises the step of dispersing said broadband output into two or more sub-bands.

34. The method of claim 33, further comprising the step of detecting an intensity of each of said two or more sub-bands.

35. The method of claim 34, wherein said step of producing said chemical absorption spectrum comprises a step of multiplexing said intensities of said two or more sub-bands.

36. The method of claim 32, further comprising the step of comparing said chemical absorption spectrum to one or more known absorption spectra.

37. The method of claim 32, further comprising the step of determining the presence of a known chemical at said remote location.

38. A flash spectroscopy chemical detection system comprising:
    means for producing a pump wave;
    means for degenerately amplifying said pump wave and producing a broadband output, wherein said broadband output has a bandwidth or linewidth with a full-width half-maximum value of about 5 percent to about 25 percent of a central broadband output wavelength;
    means for directing said broadband output to a remote location;
    means for detecting said broadband output from said remote location; and
    means for identifying a chemical agent.

39. The system of claim 38, wherein said means for identifying further comprises means for producing a chemical absorption spectrum.

40. The system of claim 38, wherein said means for identifying comprises means for dispersing said broadband output into two or more sub-bands.

41. The system of claim 40, wherein said means for identifying further comprises means for detecting an intensity of each of said two or more sub-bands.

42. The system of claim 41, wherein said means for identifying further comprises means for multiplexing said intensities of said two or more sub-bands to produce said absorption spectrum.

43. The system of claim 42, wherein said means for identifying further comprises means for correlating said absorption spectrum with a known chemical absorption spectrum.

44. The system of claim 38, wherein said broadband output has a bandwidth or linewidth with a full-width half-maximum value of greater than 200 $cm^{-1}$.

* * * * *